(12) United States Patent
Watkins

(10) Patent No.: US 10,137,081 B2
(45) Date of Patent: Nov. 27, 2018

(54) DEVICE AND METHOD FOR SUSTAINED RELEASE OF ANTIPSYCHOTIC MEDICATIONS

(71) Applicant: DELPOR, INC., San Francisco, CA (US)

(72) Inventor: Gregory Alan Watkins, Oakland, CA (US)

(73) Assignee: Delpor, Inc., San Francisco, CA (US)

( * ) Notice: Subject to any disclaimer, the term of this patent is extended or adjusted under 35 U.S.C. 154(b) by 0 days.

(21) Appl. No.: 14/432,103

(22) PCT Filed: Sep. 27, 2013

(86) PCT No.: PCT/US2013/062311
§ 371 (c)(1),
(2) Date: Mar. 27, 2015

(87) PCT Pub. No.: WO2014/052837
PCT Pub. Date: Apr. 3, 2014

(65) Prior Publication Data
US 2015/0250716 A1 Sep. 10, 2015

Related U.S. Application Data

(60) Provisional application No. 61/707,832, filed on Sep. 28, 2012.

(51) Int. Cl.
| | | |
|---|---|---|
| *A61K 9/00* | (2006.01) | |
| *A61K 31/519* | (2006.01) | |
| *A61K 31/4515* | (2006.01) | |
| *A61K 31/496* | (2006.01) | |
| *A61K 31/551* | (2006.01) | |

(52) U.S. Cl.
CPC ........ *A61K 9/0024* (2013.01); *A61K 31/4515* (2013.01); *A61K 31/496* (2013.01); *A61K 31/519* (2013.01); *A61K 31/551* (2013.01)

(58) Field of Classification Search
None
See application file for complete search history.

(56) References Cited

U.S. PATENT DOCUMENTS

| | | | |
|---|---|---|---|
| 4,038,395 A * | 7/1977 | Lassen ................ | A61K 31/495 514/252.13 |
| 4,735,804 A | 4/1988 | Caldwell et al. | |
| 7,744,918 B2 | 6/2010 | Yanaguchi et al. | |
| 9,561,352 B2 * | 2/2017 | Martin ................ | A61K 9/0024 |
| 2004/0133154 A1 | 7/2004 | Flaherty et al. | |
| 2009/0061003 A1 | 3/2009 | Hermansson et al. | |
| 2010/0022511 A1 | 1/2010 | Liu et al. | |
| 2010/0266655 A1 * | 10/2010 | Dadey ................ | A61K 9/0024 424/422 |
| 2011/0106006 A1 | 5/2011 | Martin et al. | |
| 2011/0152377 A1 | 6/2011 | Hanma et al. | |
| 2011/0223233 A1 | 9/2011 | Martin et al. | |
| 2012/0184563 A1 | 7/2012 | Hanma | |

FOREIGN PATENT DOCUMENTS

| | | |
|---|---|---|
| EP | 0196132 * | 10/1986 |
| JP | 2006-169238 A | 6/2006 |
| JP | 2010-526183 A | 7/2010 |
| WO | WO 2008/134731 A1 | 11/2008 |
| WO | WO 2010/016219 A1 | 2/2010 |
| WO | WO 2012/147035 A1 | 11/2012 |

OTHER PUBLICATIONS

Chorghade, Mukund et al., Drug Discovery and Development, (Feb. 16, 2007), pp. 1-2.*
Cameo Chemicals (May 27, 2010), pp. 1-4.*
Chemspider, Risperidone, accessed Feb. 3, 2016, pp. 1-3.*
International Search Report from PCT Patent Application No. PCT/US2013/062311 dated Dec. 2, 2013, application now published as WO2014/052837 on Apr. 3, 2014.

* cited by examiner

*Primary Examiner* — Dennis J Parad
*Assistant Examiner* — Lyndsey M Beckhardt
(74) *Attorney, Agent, or Firm* — McDermott Will & Emery LLP (57) ABSTRACT

A drug delivery device comprising a non-erodible, non-porous housing member defining a reservoir is provided. The reservoir is loaded with a dry formulation of a selected salt of a neuroleptic agent. The housing member has one or more porous partitions, where the pores of the partitions are sufficiently small to retain the insoluble powder particles within the reservoir yet large enough to allow diffusion of the active agent once the device is hydrated. A therapeutic dose of the drug is released from the device at a constant rate over a period of approximately 2-6 months.

6 Claims, 9 Drawing Sheets

DEVICE AND METHOD FOR SUSTAINED RELEASE OF ANTIPSYCHOTIC MEDICATIONS

CROSS-REFERENCE TO RELATED APPLICATIONS

This application is a U.S. National Stage of International Patent Application No. PCT/US2013/062311, filed Sep. 27, 2013, which claims the benefit of U.S. Application No. 61/707,832 filed Sep. 28, 2012, each of which is hereby incorporated by reference in its entirety.

TECHNICAL FIELD

The subject matter described herein relates to the fields of drug delivery and therapeutic agents. More precisely, the subject matter relates to an implantable drug-delivery device designed for delivery of an antipsychotic agent at a constant rate over an extended period.

BACKGROUND

For a variety of therapeutic agents, it would be desirable to deliver an active pharmaceutical ingredient (e.g., an agent or a drug) into the bloodstream of a subject from a subcutaneously implanted device at a substantially constant rate and/or over a sustained period of up to several months. For selected drugs, this delivery pattern can provide substantial clinical benefits to patients and address important unmet medical needs.

In general, there are at least two challenges that must be overcome in implementing an effective, long-term drug-delivery device of this type. First, the amount of drug delivered by the implanted device must be sufficient to provide the desired therapeutic effect and be substantially constant over time; that is, the release profile approximates zero-order kinetics, so that the treated individual receives a substantially constant therapeutic dose over a specific time period without dose spiking or periods of sub-therapeutic delivery. Secondly, the device should be capable of holding an amount of drug sufficient for releasing a therapeutic dose of compound over an extended period, e.g., 1-6 months, with a size and shape suitable for implantation in a selected anatomical site. For example, a device intended to be implanted in a subcutaneous site may have an elongate shape and a cross-sectional depth of less than about 5-6 mm so as be accommodated in the limited depth of the subcutaneous space and not to produce an unsuitably large bulge in the skin above the implantation site. In some scenarios, the device would be less than about 50 mm in overall length so that normal movement would not cause the device to erode the surrounding tissues, particularly at the ends of the device where, during normal movement, bending of the device relative to the plane of tissue may occur resulting in rupture of the device through the skin surface. Given these constraints, the maximum practical volume of the drug reservoir of a subcutaneously implanted device is generally considered to be in the range of 500 microliters (µL), assuming that substantially all of the volume enclosed by the device walls is available to serve as a drug reservoir.

An exemplary shape for a subcutaneously implantable device is cylindrical. Cylindrical devices may be implanted by placing the device in an implanter tool or trocar, an open-ended, pointed cannula with an inner diameter slightly larger than the outer diameter of the device. The trocar, loaded with the device, is inserted, through a small incision, and tunneled under the skin distally from the entry point. The device is positioned under the skin by retracting the trocar shaft mechanically, or by removing the trocar while placing pressure on the end of the device using a rod or plunger passed through the opposite end of the trocar shaft, leaving the device in place under the skin. A butterfly band-aid or surgical suture is used to close the small incision.

The foregoing examples of the related art and limitations related therewith are intended to be illustrative and not exclusive. Other limitations of the related art will become apparent to those of skill in the art upon a reading of the specification and a study of the drawings. Moreover, the discussion of the background herein is included to explain the context of the subject matter described herein. This is not to be taken as an admission that any of the material referred to was published, known, or part of the common general knowledge as at the priority date of any of the claims.

BRIEF SUMMARY

The following aspects and embodiments thereof described and illustrated below are meant to be exemplary and illustrative, not limiting in scope.

In one aspect, a drug delivery device is provided. The device comprises a non-erodible, non-porous housing member defining a reservoir, the housing member having first and second opposing ends. A porous partition is positioned in the housing member, preferably on one or both ends of the housing member, and contained within the reservoir is a drug formulation comprised of a salt of sparingly soluble drugs, in particular a salt of a free base active agent that is virtually insoluble in physiological fluids. The selected salt form provides a concentration of the ionic form of the drug, in an aqueous suspension when the drug formulation is hydrated with a physiological fluid, sufficient to provide release of a therapeutic dose of the drug from the device over a period of more than one month, as solubilized drug diffuses out of the device across the partition.

In some embodiments, the housing member is water impermeable. In other embodiments, the housing member is a metal.

In some embodiments, the porous partition is selected from a porous polymer membrane, a sintered metallic membrane, a ceramic membrane, and a glass fiber membrane, or a combination of these.

In some embodiments, the drug is a neuroleptic agent. In exemplary embodiments, the neuroleptic agent is a pharmaceutically-acceptable salt of risperidone or 9-hydroxyrisperidone, the salt form of the agent capable of providing sustained (e.g., for 30 days or more, for 60 days or more, for 90 days or more), zero-order release of the agent, as described further herein. In some embodiments, the neuroleptic agent is a salt of olanzapine, paliperidone, asenapine, haloperidol or aripiprazole, the salt form of the agent capable of providing sustained (e.g., for 30 days or more, for 60 days or more, for 90 days or more), zero-order release of the agent.

In some embodiments, the total amount of neuroleptic agent loaded in the reservoir is greater than about 100 mg. In some embodiments, the total amount of neuroleptic agent loaded in the reservoir is from about 10 mg to about 30 grams. In some embodiments, the total amount of neuroleptic agent loaded in the reservoir is from about 15 mg, about 30 mg, about 45 mg, about 100 mg, about 200 mg, about 300 mg, about 400 mg, about 500 mg, about 1 g, about 5 g, about 10 g, about 15 g, about 20 g or about 30 grams.

In some embodiments, the drug is a salt of buprenorphine, the salt form of buprenorphine capable of providing sustained (e.g., for 30 days or more, for 60 days or more, for 90 days or more), zero-order release of buprenorphine.

In some embodiments, the drug is present in soluble and insoluble forms in a total amount greater than about 100 mg/mL. In some embodiments, the drug is present in soluble and insoluble forms in a total amount between about 100 mg/mL and about 5000 mg/mL, or 100 mg/mL to 30 g/ml. In some embodiments, the drug is present in soluble and insoluble forms in a total amount of at least about 15 mg/mL, at least about 30 mg/mL, at least about 45 mg/mL, at least about 100 mg/mL, at least about 200 mg/mL, at least about 300 mg/mL, at least about 400 mg/mL, at least about 500 mg/mL, at least about 1 g/mL, at least about 5 g/mL, at least about 10 g/mL, at least about 15 g/mL, at least about 20 g/mL or at least about 30 g/ml. In other embodiments, the drug is present in the device in a total amount of between about 15-500 mg/mL, 10-1000 mg/mL, 5-5000 mg/mL, 5-500 mg/mL, 5-1000 mg/mL, or 15-1000 mg/mL.

In another aspect, a method for delivering a sparingly water-soluble drug from an aqueous suspension into an environment of use is provided. The method comprises combining the free base of the sparingly water-soluble drug with a 5-, 6-, 7-, 8-, 9- or 10-carbon aliphatic acid to form a salt of the drug, wherein the salt form of the drug maintains a substantially constant concentration of solubilized drug in the aqueous suspension to achieve sustained release of a therapeutic amount of the drug into an environment of use for a period of at least about one week to at least about 30 days.

In some embodiments of the device and methods, the aliphatic fatty acid is a 5- to 9-carbon aliphatic acid. In some embodiments, the aliphatic acid has not more than 9 carbons. In some embodiments, the aliphatic acid is a carboxylic acid with 5, 6, 7 or 8 carbon atoms, and in another embodiment the aliphatic fatty acid is a straight chain carboxylic acid with 5, 6, or 8 carbon atoms. In another embodiment, the counterion of the drug salt is pentanoic acid, hexanoic acid, heptanoic acid, or octanoic acid, or a mixture thereof.

In another aspect, a method of treating a patient is provided. The method comprises providing a device as described herein, and implanting the device in the patient. In some embodiments, the method is for treating a patient suffering from a psychotic disorder, wherein the drug is a neuroleptic agent and is delivered at a substantially constant release rate for between about 1-6 months. In some embodiments, the device is implanted subcutaneously.

In another aspect, an implantable device for use in releasing a therapeutic agent at an implantation site in a subject, at a substantially constant release rate over a selected time period between about 1-6 months, is provided. The device comprises, in operative condition, a housing that defines an interior chamber, the housing formed of a non-erodible, non-porous material; a partition affixed or connected to the housing, the partition comprising a plurality of pores which allow a therapeutic agent in a soluble form (but not in an insoluble form) to diffuse out of the chamber into an external medium; and contained within the chamber, in operative condition when the chamber is hydrated, an aqueous suspension of a salt form of a poorly water soluble therapeutic agent, said salt form sufficient to provide a therapeutic dose of the drug over a selected time period, as the soluble agent form diffuses out of the device across the partition by means of a concentration gradient between the chamber and the environment of use.

In some embodiments, the device is cylindrical in shape, and its outer surface is devoid of pits, ridges or pores. One or both of the circular cylinder ends is fitted with the porous partition, and the overall outer surface area of the device is less than about 7 $cm^2$. In some embodiments, the overall outer surface area of the device is between about 0.01 $cm^2$ and about 10 $cm^2$. In some embodiments, the overall outer surface area of the device is about 0.1 $cm^2$, about 1 $cm^2$, about 2 $cm^2$, about 3 $cm^2$, about 4 $cm^2$, about 5 $cm^2$, about 6 $cm^2$, about 7 $cm^2$, about 8 $cm^2$, about 9 $cm^2$, or about 10 $cm^2$.

In another aspect, an implantable device for use in releasing a therapeutic agent at an implantation site in a subject, at a substantially constant release rate over a selected time period between about 1-6 months, is provided. In some embodiments, the therapeutic agent is released over a time period selected from 1-2 days, 1-3 days, 1-4 days, 1-5 days, 2-3 days, 2-4 days, 2-5 days, 2-6 days, 3-4 days, 3-5 days, 3-6 days, 4-5 days, 4-6 days, or 5-6 days. In some embodiments, the therapeutic agent is released over a selected time period of about 30-180 days, 30-40 days, 30-45 days, 30-60 days, 30-90 days, 30-100 days, 30-120 days, 40-180 days, 40-45 days, 40-60 days, 40-90 days, 40-100 days, 40-120 days, 45-180 days, 45-60 days, 45-90 days, 45-100 days, 45-120 days, 60-180 days, 60-90 days, 60-100 days, 60-120 days or more. The device comprises an interior reservoir defined by a housing member, and contained within the reservoir a therapeutic agent. The device also comprises a partition separating the reservoir from an external medium, the partition containing multiple pores which allow therapeutic agent in soluble form (but not in insoluble form) to diffuse out of the reservoir into the external medium. In some embodiments, the pores occupy less than about 1.7 $cm^2$ of the total surface of the chamber. Contained within the reservoir, in operative condition when the reservoir is hydrated, is an aqueous suspension comprised of a salt form of the therapeutic agent sufficient to drive outward flux of a therapeutic dose of the agent.

In some embodiments, the salt form of the active agent is selected to dissolve or hydrolyze at a rate that corresponds to the intended period of operation of said device.

In another aspect, a drug delivery device comprised of a non-erodible, non-porous housing member defining a reservoir is provided. The hosing member has first and second opposing ends, and a porous partition is positioned in the housing member. Contained within the reservoir is a drug formulation comprised of a salt form of a neuroleptic agent (also referred to as an antipsychotic agent, in some embodiments), the salt form of the neuroleptic agent capable of providing a concentration of the neuroleptic agent in the reservoir such that when the drug formulation is hydrated the neuroleptic agent is released at a rate that provides a therapeutic dose of the neuroleptic agent over a period of at least about 30 days.

In one embodiment, the neuroleptic agent is risperidone, 9-hydroxyrisperidone, olanzapine, paliperidone, asenapine, haloperidol or aripiprazole.

In another embodiment, the salt form of the neuroleptic agent comprises a counterion, the counterion comprising an aliphatic carboxylic acid with 5-8 carbon atoms. In another embodiment, the aliphatic carboxylic acid comprises a straight carbon chain, a branched chain or a mixture thereof. Exemplary aliphatic carboxylic acids are, in some embodiments, pentanoic acid, hexanoic acid, heptanoic acid, octanoic acid and mixtures thereof. In one embodiment, the carboxylic acid comprises a functional group that increases, relative to a carboxylic acid without the functional group, the aqueous solubility of the salt form of the neuroleptic agent. In yet another embodiment, the carboxylic acid is mandelic acid. In another embodiment, the counterion of the drug salt is a straight chain carboxylic acid with 5, 6, or 8 carbon atoms.

In one embodiment, the salt form of the neuroleptic agent is risperidone octanoate, risperidone hexanoate or risperidone pentanoate.

In another embodiment, the therapeutic dose is between about 0.8-2.5 mg/day and risperidone is released from the device for a period of between about 2-6 months.

In still another embodiment, risperidone is released at a substantially zero-order rate of release. In another embodiment, risperidone is released at a substantially zero-order rate of release for a period of at least about 30 days, 60 days, 90 days, or 120 days.

In other embodiments, the porous partition is positioned in one or both ends of the housing member. In another embodiment, the housing member is a cylindrical titanium tube. In one embodiment, the housing has an outer diameter ranging from 4.0 mm to 5.5 mm, an inner diameter ranging from 3.5 mm to 5.0 mm, and a length ranging from 4.0 to 5.0 cm.

In one embodiment, the porous partition is positioned at both ends of the reservoir. In another embodiment, the porous partition is comprised of sintered titanium fits or is comprised of a polymeric membrane. In another embodiment, the porous partition has pores with a pore size less than 5 microns.

In another aspect, a method for delivering a neuroleptic agent to a subject in need of treatment is provided, the method comprising implanting a device as described herein. In one embodiment, the device is implanted subcutaneously. In one embodiment, the method is provided to a subject suffering from a mental disorder. In other embodiments, the method provides for treatment of schizophrenia, bipolar disorder, psychotic depression, or Tourette's syndrome.

In another aspect, a method for extended delivery of a neuroleptic agent to a subject in need of treatment is provided, by implanting a device as described herein.

In one embodiment, the agent is released into an environment of use, such as a subcutaneous compartment of a human subject, for a period of greater than or equal to 60 days.

Additional embodiments of the present methods will be apparent from the following description, drawings, examples, and claims. As can be appreciated from the foregoing and following description, each and every feature described herein, and each and every combination of two or more such features, is included within the scope of the present disclosure provided that the features included in such a combination are not mutually inconsistent. In addition, any feature or combination of features may be specifically excluded from any embodiment of the present disclosure. Additional aspects and advantages of the present disclosure are set forth in the following description and claims, particularly when considered in conjunction with the accompanying examples and drawings.

DETAILED DESCRIPTION

I. Definitions

Various aspects now will be described more fully hereinafter. Such aspects may, however, be embodied in many different forms and should not be construed as limited to the embodiments set forth herein; rather, these embodiments are provided so that this disclosure will be thorough and complete, and will fully convey its scope to those skilled in the art.

Where a range of values is provided, it is to be understood that each intervening value, to the tenth of the unit of the lower limit unless the context clearly dictates otherwise, between the upper and lower limits of that range and any other stated or intervening value in that stated range is also specifically encompassed within the disclosure. For example, if a range of 1-6 days is stated, it is intended that 1 day, 2 days, 3 days, 4 days, 5 days, and 6 days are also explicitly disclosed. Furthermore, each smaller range between any stated value or intervening value in a stated range and any other stated or intervening value in that stated range is encompassed within the disclosure. The upper and lower limits of these smaller ranges may independently be included or excluded in the range, and each range where either, neither or both limits are included in the smaller ranges is also encompassed within the disclosure, subject to any specifically excluded limit in the stated range. Where the stated range includes one or both of the limits, ranges excluding either or both of those included limits are also included in the disclosure.

As used in this specification, the singular forms "a," "an," and "the" include plural referents unless the context clearly dictates otherwise. Thus, for example, reference to an "excipient" includes a single excipient as well as two or more forms of the same or different excipients, and the like.

The term "aqueous suspension" refers to a solid material dispersed in a liquid solvent that is substantially water.

The terms "therapeutic agent," "drug," "active pharmaceutical ingredient" or "API" refer to a biological or chemical agent used in the treatment of a disease or disorder, or to treat or alleviate symptoms associated with a disease or disorder.

The term "therapeutic window" refers to the dose range of the active pharmaceutical ingredient released from the device in vitro predicted to provide sufficient in vivo bioavailability to provide efficacy while minimizing side effects in patients.

The term "precipitate" or "insoluble form" refer to a solid substance that separates from a solution.

The term "substantially zero-order" means that over a medically acceptable percentage of the dose of a therapeutic agent provided in a drug delivery device, the rate of release of the agent is approximately constant.

Any publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed. All references are herein incorporated by reference in their entireties.

II. General Overview of the Drug Delivery Device

The drug delivery device described herein comprises a non-erodible, non-porous housing member defining a reservoir, which is, in some embodiments cylindrical in shape. The reservoir is loaded with a dry powder formulation of a salt of a neuroleptic agent. Porous partitions, such as polymer membranes or sintered metal fits, are sealed to the housing, and in one embodiment to one or both ends of the reservoir. The nominal pore size of the partitions is sufficiently small so as to retain the insoluble powder particles within the reservoir, but large enough to allow diffusion of the active agent once the drug formulation is hydrated, typically with a physiologic fluid. The formulation loaded into the reservoir is a drug formulation comprised of a salt of a sparingly water-soluble drug, in particular a salt of a free base active agent that is virtually insoluble in physiological fluids, such as risperidone. As will be illustrated by the data discussed herein, the salt form of the insoluble drug is chosen (selected) to provide a concentration of the ionic form of the drug, in an aqueous suspension when the drug formulation is hydrated, sufficient to provide release of a therapeutic dose of the drug from the device over a period of more than one month, as solubilized drug diffuses out of the device across the partition. In one embodiment, device enables the delivery of the drug at a constant rate over a period of 2-6 months.

A. Drug Delivery Device

In a first aspect, a device for use in releasing a therapeutic agent into an environment of use is provided. The therapeutic agent may be the salt of a sparingly water soluble base. The device, for reasons described hereinbelow, is capable of providing a substantially constant release rate of the drug over an extended time period. The device is of a size, shape and/or has surface properties to be suitable for subcutaneous implantation and explantation. The device includes an interior chamber separated from an external medium in an environment of use by a porous partition, and contained within the chamber, when the device is in use, is an aqueous suspension of the loaded drug salt.

The housing member may be formed from a biocompatible material, and a skilled artisan will readily identify suitable materials, including but not limited to metals, such as titanium; ceramics, such as alumina, silica, and polymers. An exemplary shape of the housing member is cylindrical. Skilled artisans, however, will understand that alternative geometrical shapes may also be suitable, and these shapes are contemplated. In some embodiments, a tubular section of the cylindrical housing member has a non-porous, smooth, and/or liquid impermeable outer surface. For example, a tubular section of housing member may be formed of titanium and finished on its outer surface, i.e., the surface of device in contact with the environment of use, has a satin, mirror, or other polish. To insure the safe and medically uncomplicated use and removal of the device, its outer surface may be smooth, devoid of pits, ridges and pores. Rough or porous surfaces may provoke a tissue response during the implantation period. Tissue in-growth, attachment or adherence of matrix components or cellular processes or pseudopodia to pits or pores on the surface of the device can complicate removal and possibly even tear the ingrown tissue upon removal, causing trauma to the site. Smooth surfaced cylindrical devices, on the other hand, provoke little or no tissue in-growth and/or are easily removed from the implantation site by simply reopening the incision made during implantation and pushing the distal end of the device with one's fingers through the skin, forcing the device to emerge from the incision. Accordingly, in some embodiments, the housing member is non-porous, and in some embodiments the housing member is water-impermeable, non-erodible and/or non-swelling.

While a skilled artisan can appreciate that the dimensions of the drug delivery device can be selected according to the site of implantation and desired loading of drug, and that the dimensions of the device are not critical to the invention described herein, a working example is a device with an outer diameter from 4.0 mm to 5.5 mm, an inner diameter in the range of 3.5 mm to 5.0 mm, and overall length from 4.0 to 5.0 cm.

As mentioned, the device is intended to be implanted into an anatomical site in a subject, and implanted at a subcutaneous site. Following implantation, the local concentration of the drug in the external medium is maintained at virtually zero at all times by diffusion and the continuous movement (bulk flow) of interstitial fluid around the device. In operation, a concentration gradient is established between the soluble form of the drug or agent within the reservoir and the external medium. The gradient serves to drive diffusion of the soluble form of the agent from the reservoir through the porous partition into the external medium. A steady state is established between the insoluble fractions and soluble fraction of the agent within the reservoir and a released fraction which enters the external medium and is immediately washed away into the systemic circulation. As the soluble form of the agent moves from the device reservoir, through the porous partition and into the external medium under the influence of the concentration gradient, insoluble agent in the formulation contained in the device reservoir dissolves, replacing that which has been released. It should be noted that the concentration gradient of the ionic/protonated form of the drug may be coupled to a pH gradient between the interior and exterior of the device. In the specific example of a basic drug, efflux of the molecule from the device (as a cation) will be maximized when the pH within the device is less than the pH outside of the device, which is assumed to be approximately 7.4 in most environments of use. In this manner a constant concentration gradient is maintained and a constant outward flux of agent is maintained according to Fick's law.

The porous partition in the device may be composed of a ceramic (such as alumina or silica), a metal (such as sintered titanium or stainless steel), an organic polymer (such as polyvinylidene fluoride or a cellulose ester), or two or more of these matrices arranged in tandem. The pore size of the porous partition (also referred to as a membrane) is selected to retain insoluble drug particles within the reservoir while allowing the diffusion of soluble forms of the drug across the membrane. For example, where the smallest particle size of the granulated salt from of the neuroleptic agent loaded into the device is 20 microns, a membrane with a nominal size exclusion of less than 5 microns would be suitable. In some embodiments, the chosen membrane configurations enable efflux of the protonated drug from the device, but are sufficiently restrictive to retain undissolved particles of the salt.

B. Drug Formulation

It is well-appreciated that risperidone (along with many other psychiatric drugs that must cross the blood-brain barrier) is extremely insoluble in water as the free base. Because of this, risperidone alone cannot create a sufficient concentration gradient across a membrane to drive therapeutic levels of drug output by Fickian (passive) diffusion across a membrane.

In some embodiments, a solution to this problem is provided providing in the reservoir of the device a salt form of the water-insoluble drug. Many organic salts of water-insoluble drugs, for example risperidone, (e.g., the lactate, glycolate, tartrate and acetate) as well as many inorganic salts (e.g., the hydrochloride) are highly soluble—so much so that they exit rapidly from the device, and thus complicate the design of a long-lasting implantable device. Other organic salts (e.g., the decanoate or dodecanoate) are derived from acids that are insoluble in water to begin with, and consequently, the resulting salts are not appreciably more soluble than the free base form of the water-insoluble drug. However, a small range of organic acids, including but not limited to simple aliphatic carboxylic acids containing 5-8 carbons, have a limited (but measurable) baseline solubility in water. These acids create salt forms of the water-insoluble drugs with similarly modest baseline solubilities that are still greatly enhanced relative to free base form of the drug. The theoretical advantages of these salts for implant applications are numerous, and include, but are not limited to, the following:

1.) Straight-chain aliphatic acids in this class occur naturally and are expected to have a safe toxicological profile. In some cases, at least one branched-chain acid (e.g., 2-propylpentanoic acid, or valproic acid) may be an inexpensive, well-tolerated drug in patients at far higher doses than intended to employ in patients, and can be sourced as pharmaceutical-grade material.

2.) The acid and free base form of the drug (e.g., risperidone) are reacted together before loading into the device, and thus there is no kinetically inefficient, heterogeneous activation step. Such steps are sensitive to mixing effects, producing less reproducible outputs in a dynamic in vivo environment.

3.) The density of a salt and its compressibility limit the mass of salt that can be loaded into a device reservoir of fixed volume. Consequently, the molar mass ratio between the drug and its counterion must be sufficiently high that sufficient drug equivalents can be compacted within the device to supply a therapeutic dose of the drug for a medically useful period of time. This requirement excludes the use of larger acids that would displace risperidone mass equivalents from the limited interior volume of the reservoir.

4.) Excess equivalents of these "privileged" salts can be efficiently loaded into the device to extend the release of a therapeutic dose range over 3-6 months via a "sacrificial salt" effect. Salts formed from weak organic acids likely react with incoming buffer components inside the device to maintain a favorably acidic pH relative to the exterior and to the first pKa of protonated drug; in this scenario, some fraction of the dissolving salt acts as an excipient to drive the release of the remainder. This effect requires that a small quantity of the drug (e.g., risperidone) will precipitate/crystallize within the drug reservoir over extended period of time, without exiting into the environment. This "sacrificial salt" effect likely boosts output in the absence of other excipients, and is expected to enhance the effective concentration gradient, and thus the release rate, of the diffusing form of the drug by Fick's Law.

5.) By varying the hydrocarbon chain length within the organic acid and/or by including suitable functional groups, it is possible to tune the solubility of the resulting salt form of the drug over a wide range. "Privileged salts" generate a concentration of dissolved drug species much higher than that achievable with the free base alone, and also maintain a reasonably constant pH and dissolution rate as drug equivalents exit the device.

6.) Mixtures of salts may be mixed to refine the release rate and duration.

Accordingly, in one embodiment, the drug formulation contained in the reservoir of the device is a salt of an antipsychotic agent. The salt of the agent comprises a counterion, and in one embodiment, the counterion comprises an aliphatic carboxylic acid with 5-8 carbon atoms. The aliphatic carboxylic acid may comprise a straight carbon chain, a branched chain or a mixture thereof. Exemplary aliphatic carboxylic acids include, but are not limited to, pentanoic acid, hexanoic acid, heptanoic acid, octanoic acid and mixtures thereof. In one embodiment, the carboxylic acid comprises a functional group that increases, relative to a carboxylic acid without the functional group, the aqueous solubility of the salt form of the neuroleptic agent.

Exemplary salts are prepared by reacting the free base of the neuroleptic agent with a carboxylic acid of 5-8 carbon atoms in a compatible organic solvent. The 5- to 8-carbon carboxylic acid can be saturated or unsaturated, branched, straight-chain or cyclic, having the stated number of carbon atoms (i.e., $C_5$-$C_8$ means five to eight carbon atoms). In some embodiments, the carboxylic acid is a straight-chain carboxylic acid such as pentanoic acid (valeric acid), hexanoic acid (caproic acid), heptanoic acid (enanthic acid), or octanoic acid (caprylic acid). The carboxylic acid may contain at least 5, at least 6, at least 7, or at least 8 carbons, and fewer than 9 carbon atoms, and one or more functional groups intended to increase aqueous solubility or crystallinity of the resulting salt, such as mandelic acid. Mixtures of salts formed from the carboxylic acids may also be used.

In one embodiment, the reservoir loaded with the dry powder of the selected salt of a neuroleptic agent is placed in a standard lyophilizer and the vial sealed under vacuum. Immediately before use, the powder is hydrated by introducing an appropriate sterile buffer into the vial; the buffer is drawn into the reservoir and hydrates the power in situ. When placed in buffer in vitro and implanted in vivo, the drug is released from the reservoir by diffusion through the porous partitions positioned at one or both ends of the reservoir at a therapeutic dose rate, which, in the case of risperidone is between 0.8-2.5 mg/day. The device enables the delivery of the drug at a constant rate over a period of 2-6 months.

C. Exemplary Devices and Method of Treatment

Studies conducted to demonstrate sustained release of a salt form of an antipsychotic agent are described in Examples 1-9. In the studies, risperidone was used as a model antipsychotic agent, and salt forms of the agent were prepared as described in Example 1. The salt form of the agent was loaded into the reservoir of a drug delivery device, which was then closed with a porous partition or membrane by a process described in Example 2. The devices were tested in an in vitro assay (Example 3) or in vivo in rats.

Figure 1:
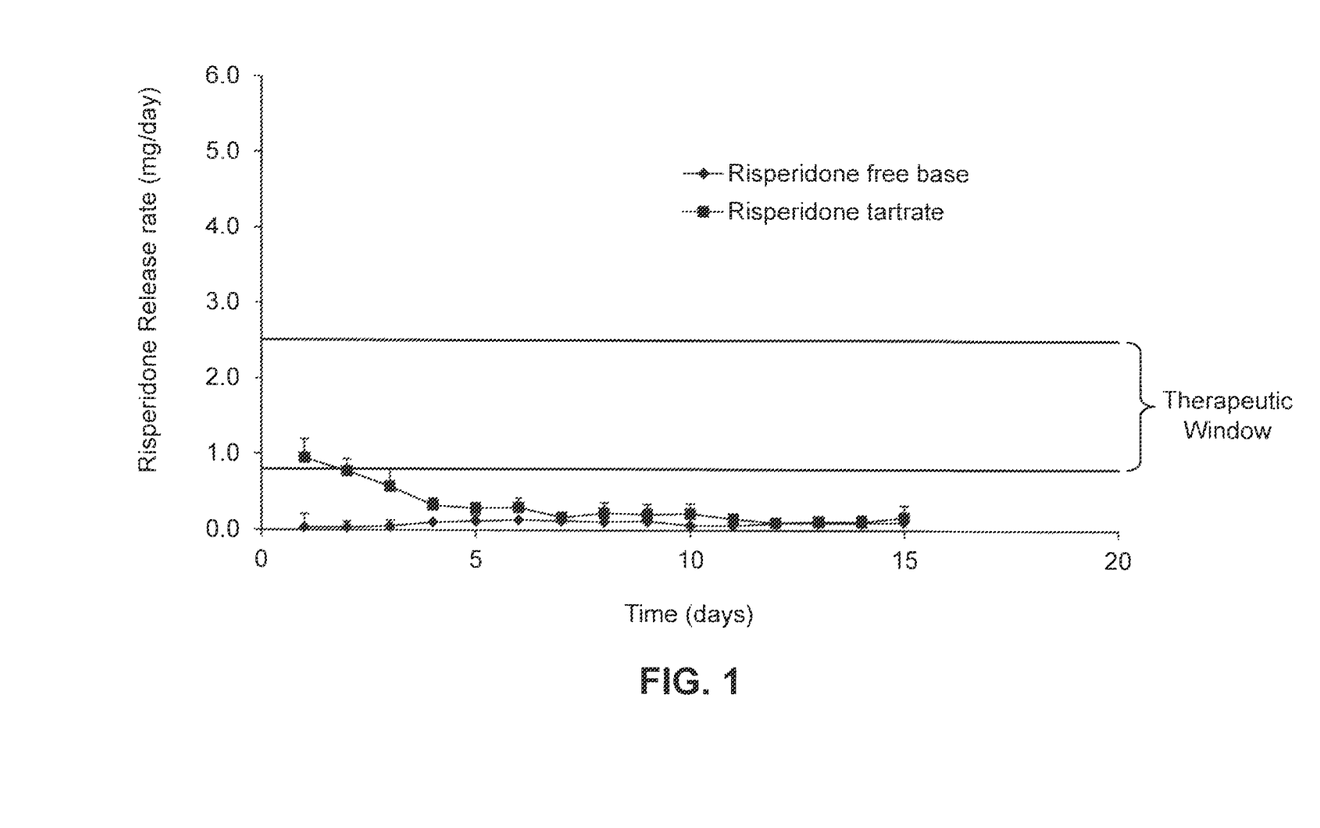
FIG. 1 is a plot comparing the release of risperidone tartrate (squares) and risperidone free base (diamonds), in mg/day, as a function of time, in days, from a device as described herein in an in vitro assay. The therapeutic window labeled in the figure represents the drug output required for efficacy while minimizing side effects and, as indicated in the figure, is between 0.8 mg/day and 2.5 mg/day.

Comparative Example 4 describes a study where release of risperidone in vitro was measured from devices comprising the free base form of the drug and the butanoate, benzoate, valproate and tartrate salt forms of the drug. Release of risperidone tartrate (squares) and of the free base form of risperidone (diamonds) are shown in FIG. 1. The therapeutic window, as indicated in the figure, represents upper and lower concentrations required for therapeutic efficacy of risperidone while minimizing side effects and is between 0.8 mg/day and 2.5 mg/day. Although the output of the tartrate salt is greater than that of the free base form of the drug, release of both forms fall well below the level needed to sustain therapy (0.8 mg/day).

Figure 2:
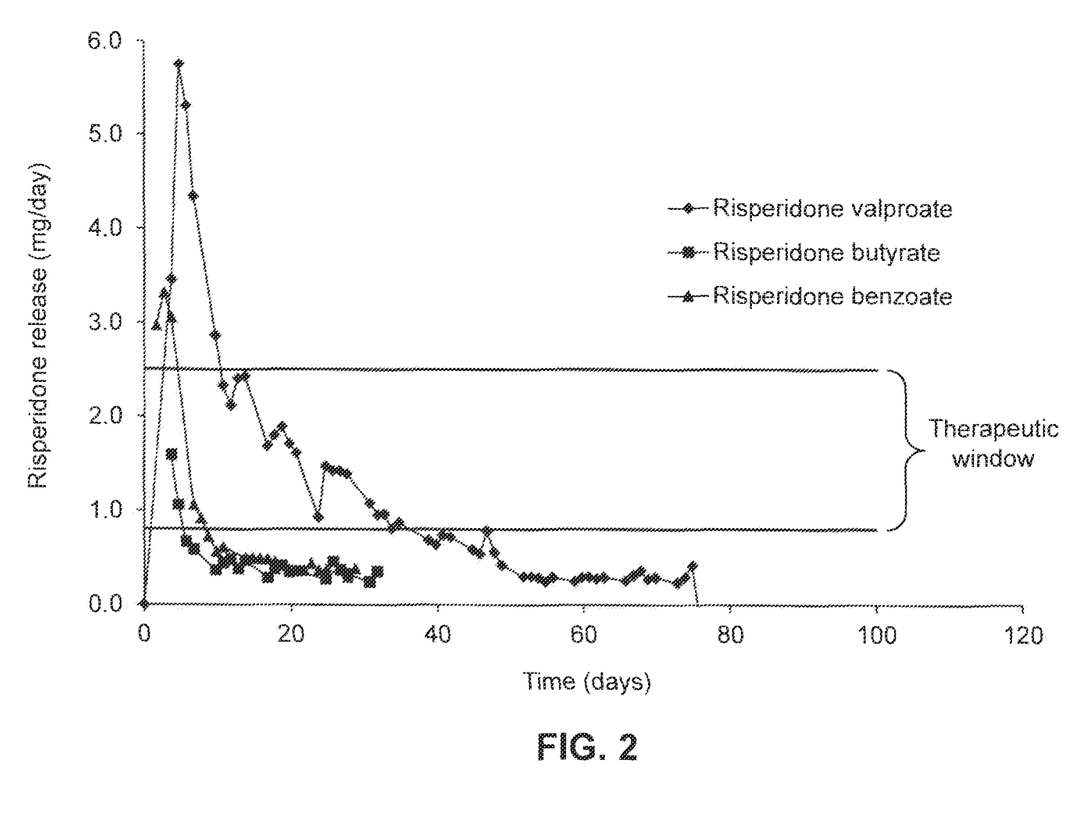
FIG. 2 is a plot of risperidone release, in mg/day, as a function of time, in days, for two salt forms of risperidone which fail to maintain therapeutic levels for ≥40 days—risperidone butyrate (square) and risperidone benzoate (triangles) from a device as described herein in an in vitro assay. Release of risperidone valproate (diamonds) from a device as described herein in an in vitro assay is also shown. The therapeutic window labeled in the figure represents the drug output required for efficacy while minimizing side effects and, as indicated in the figure, is between 0.8 mg/day and 2.5 mg/day.

Release of risperidone from devices comprising other salt forms of risperidone, valproate, benzoate and butyrate, is shown in FIG. 2. As with the tartrate form of the drug, release of risperidone from devices filled with risperidone butyrate (square) and risperidone benzoate (triangles) is insufficient to maintain therapeutic levels of the drug for a desired time period of 30 days for more. Release of risperidone from devices filled with risperidone valproate (diamonds) initially exceeded the upper desired concentration of the therapeutic window, and then fell outside the lower desired concentration limit by about day 40 of the in vitro test. The data in FIG. 2 illustrates that the in vitro release of risperidone from devices filled with risperidone valproate, risperidone benzoate and risperidone butyrate fall below the minimum therapeutic concentration in less than 40 days and are therefore of little clinical value for the intended long-term maintenance therapy of patients with schizophrenia and bipolar disorder. Moreover, the output pattern of the risperidone valproate and risperidone benzoate devices may present safety hazards if used in vivo. In both cases the output rises to high levels before falling. The spike may provoke side effects and the tail falls below the therapeutic level quickly. The output of risperidone from devices filled with risperidone butyrate reached therapeutic levels for only a few days and, thus, would be unsatisfactory for long term maintenance enabled here.

Figure 3:
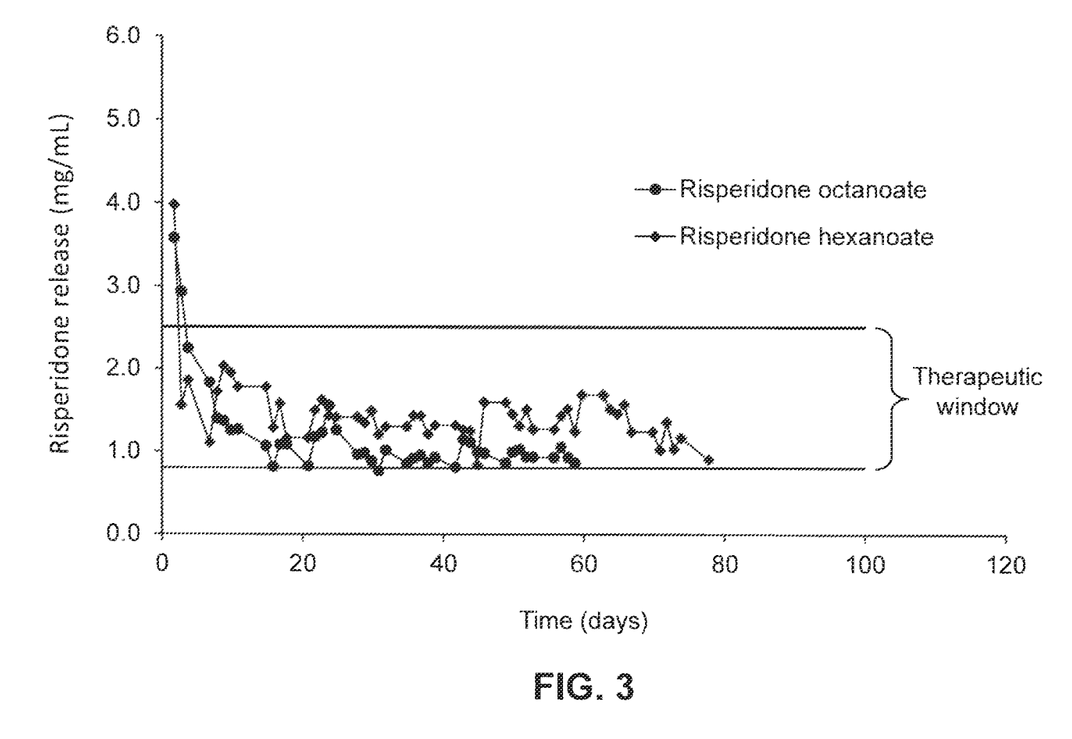
FIG. 3 is a plot of risperidone release in mg/day, as a function of time, in days, for selected salt forms of risperidone, risperidone octanoate (circles) and risperidine hexanoate (diamonds), from devices as described herein in an in vitro assay. The therapeutic window labeled in the figure represents the drug output required for efficacy while minimizing side effects and, as indicated in the figure, is between 0.8 mg/day and 2.5 mg/day.
Figure 4:
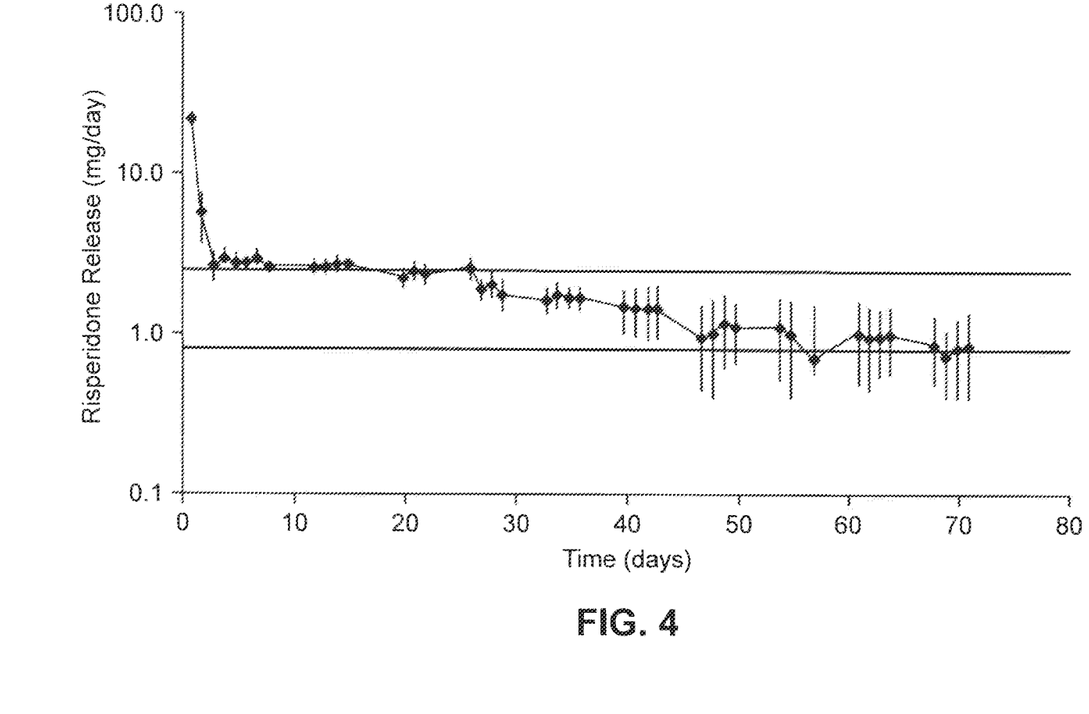
FIG. 4 is a plot of risperidone release in mg/days as a function of time, in days, of risperidone from a device loaded with risperidone pentanoate, which maintains therapeutic output for ≥60 days in an in vitro assay.

Example 5 details another study, where devices were prepared with formulations of risperidone pentanoate, risperidone hexanoate, and risperidone octanoate. In vitro release of risperidone from the devices was measured and the results are presented in FIGS. 3 and 4. The in vitro release of risperidone from devices containing risperidone hexanoate (diamonds) and risperidone octanoate (circles) is maintained within the therapeutic concentration window (0.8 mg/day to 2.5 mg/day) for a period of at least about 30 days, and in other embodiments for a period of 30 days or more, or 60 days or more (FIG. 3). FIG. 4 shows that the in vitro output from devices loaded with risperidone pentanoate is slightly above the therapeutic window for the first two weeks and thereafter the release of risperidone is a constant, zero-order release for a period of at least about 60 days.

Figure 5:
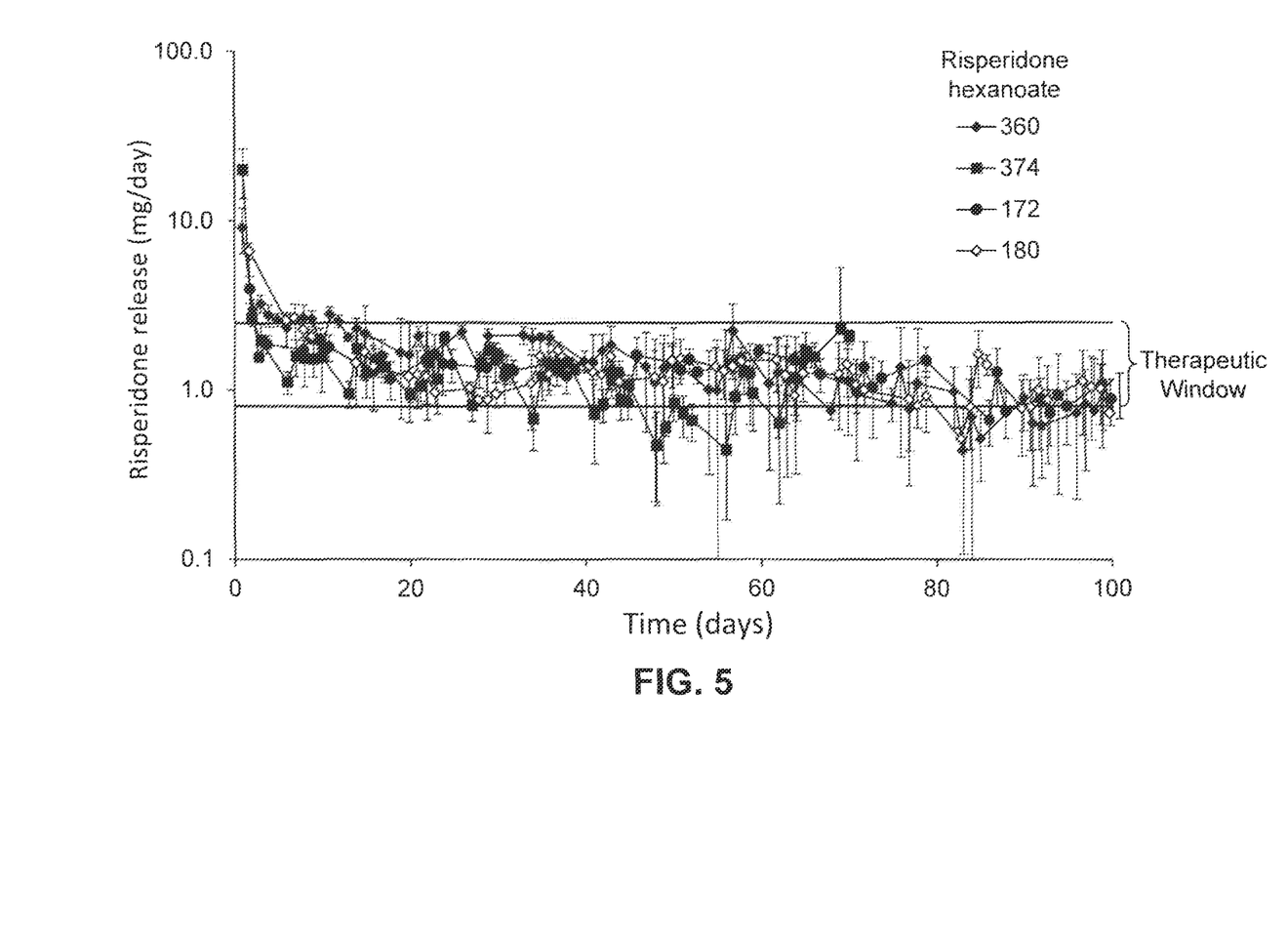
FIG. 5 is a plot of risperidone release in mg/days as a function of time, in days, of risperidone from four devices (designated by individual device numbers 172, 180, 360 and 364) containing risperidone hexanoate; the device maintain therapeutic output levels for ≥90 days.

Additional in vitro studies were conducted to measure the release of risperidone from devices containing the hexanoic acid salt of risperidone, risperidone hexanoate (Example 6). In vitro release of risperidone from four devices, identified as device numbers 172, 180, 360 and 374, each loaded with risperidone hexanoate, was measured for 90-100 days using the in vitro release assay described in Example 3. The release data is shown in FIG. 5, where it is seen that devices comprising a salt form of risperidone (e.g., risperidone hexanoate) achieve zero-order release of risperidone at a therapeutic dose or level for a period of at least about 30-60 days, or, stated alternatively, for at least about 30-90 days.

Figure 6:
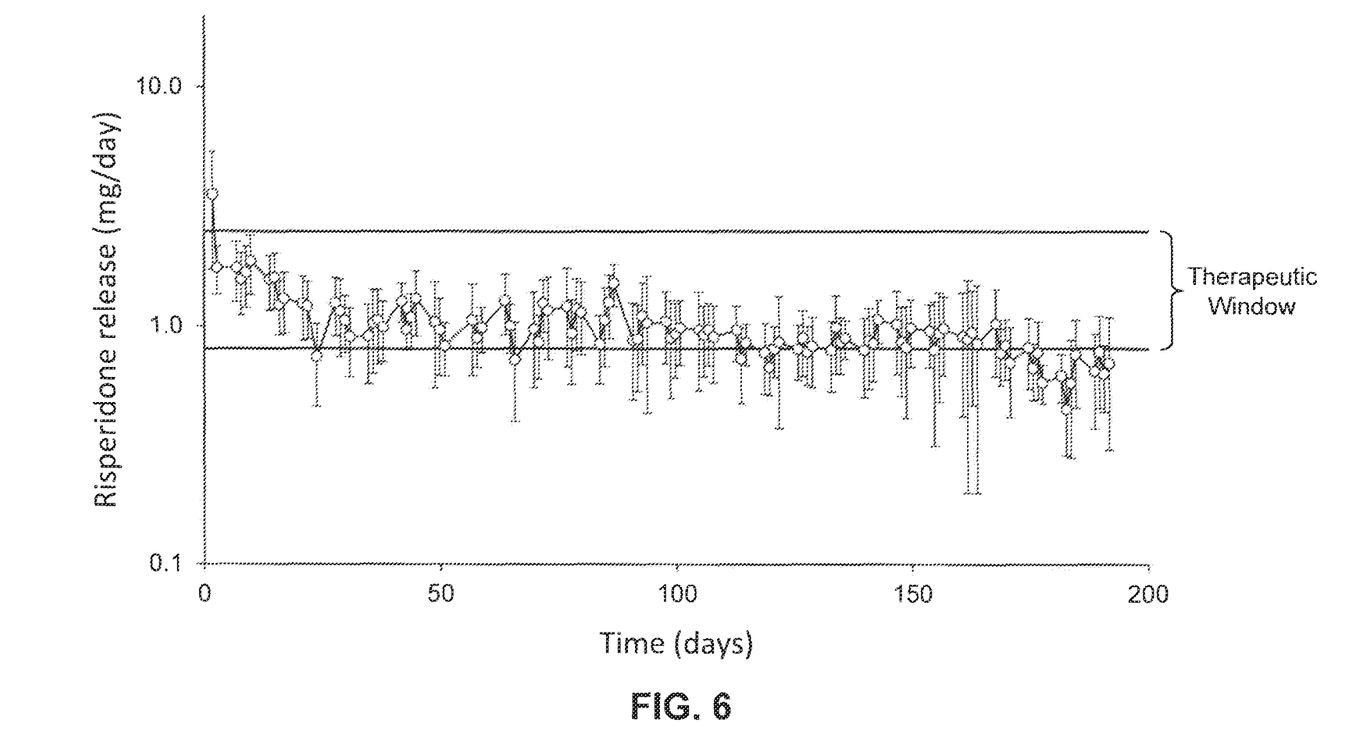
FIG. 6 is a plot of risperidone release in mg/days as a function of time, in days, of risperidone from a device comprising risperidone hexanoate; the device maintains a therapeutic in vitro output of risperidone for about 6 months.

In another study, set forth in Example 7, devices containing the risperidone hexanoate were prepared and the in vitro release of risperidone was measured for 6 months using the in vitro release assay described in Example 3. The results are shown in FIG. 6. Devices comprising a salt form of the neuroleptic agent risperidone, where the salt form comprises a hexanoic acid counterion, release risperidone at a constant, substantially zero-order rate for six months. Accordingly, in one embodiment, devices comprising a salt form of a neuroleptic agent are provided, where the salt form of the agent has a counterion that is selected to provide, and is capable of providing, a sustained, substantially zero-order rate of release of the agent for a period of between 1-6 months, alternatively from 2-6 months, alternatively from 3-6 months.

Devices containing in the drug reservoirs formulations with the hexanoate and pentanoate forms of risperidone were prepared and implanted subcutaneously in rats, to measure release in vivo (Example 8). Blood for pharmacokinetic samples was collected via tail vein at determined time points (see the table in Example 8), and the plasma was assayed for risperidone and 9-hydroxyrisperidone concentration. Plasma concentrations were normalized to initial body weight for each time point and plotted versus time. The results are shown in FIGS. 7-8.

Figure 7:
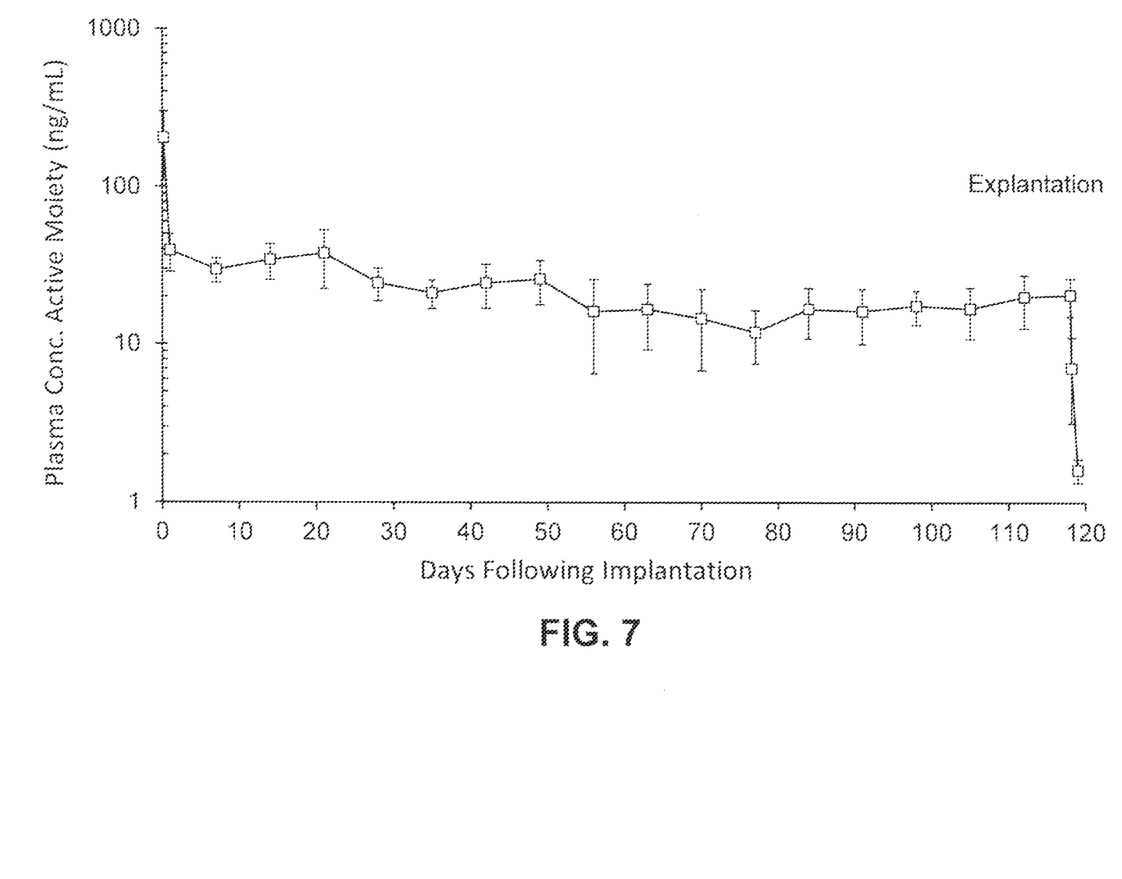
FIG. 7 is a plot of plasma concentration of risperidone and 9-OH risperidone, in ng/mL, as a function of days following implantation in rats (n=6) with a device loaded with risperidone hexanoate, where a constant plasma level of the active moiety (risperidone and 9-OH risperidone) was observed for about four months. The plasma levels falls to below the detection limit of the assay within hours of explantation of the devices at about 120 days.

FIG. 7 shows the plasma concentration of risperidone and 9-OH risperidone in rats with an implanted device loaded with risperidone hexanoate. Following a small burst of drug at the 4 hour time point, the plasma level of active moiety (risperidone plus 9-OH risperidone) remained constant (at about 20 ng/mL) for a period of about 4 months, when the device was removed. Following removal of the device, the plasma level immediately fell to below the LLQ (0.5 ng/mL).

Figure 8:
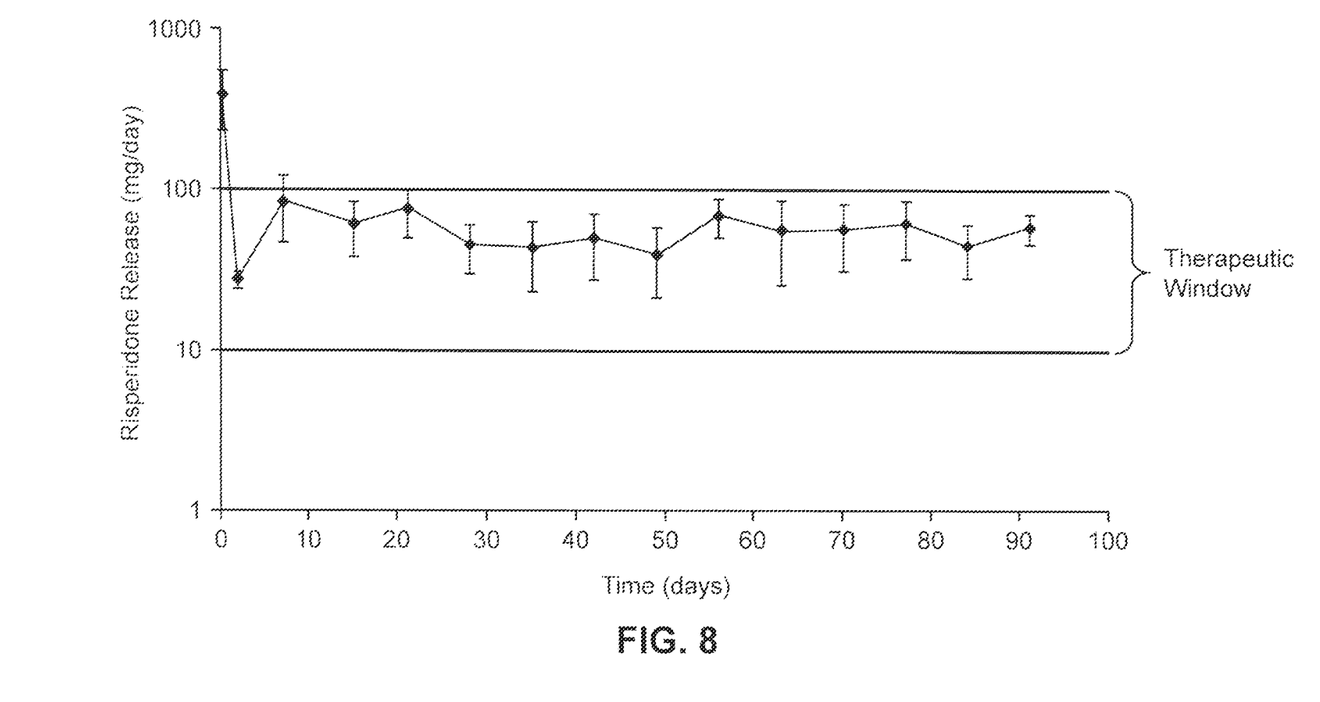
FIG. 8 is a plot of plasma concentration of risperidone and 9-OH risperidone, in ng/mL, as a function of days following implantation in rats (n=6) with a device loaded with risperidone pentanoate that shows constant plasma levels of active moiety (risperidone and 9-OH risperidone) for ≥60 days (60 days or more).

FIG. 8 shows the plasma concentration of risperidone and 9-OH risperidone in rats with an implanted device containing with risperidone pentanoate. Devices containing this salt form of drug provided a constant plasma levels of active moiety (risperidone and 9-OH risperidone) for greater than 60 days.

Figure 9:
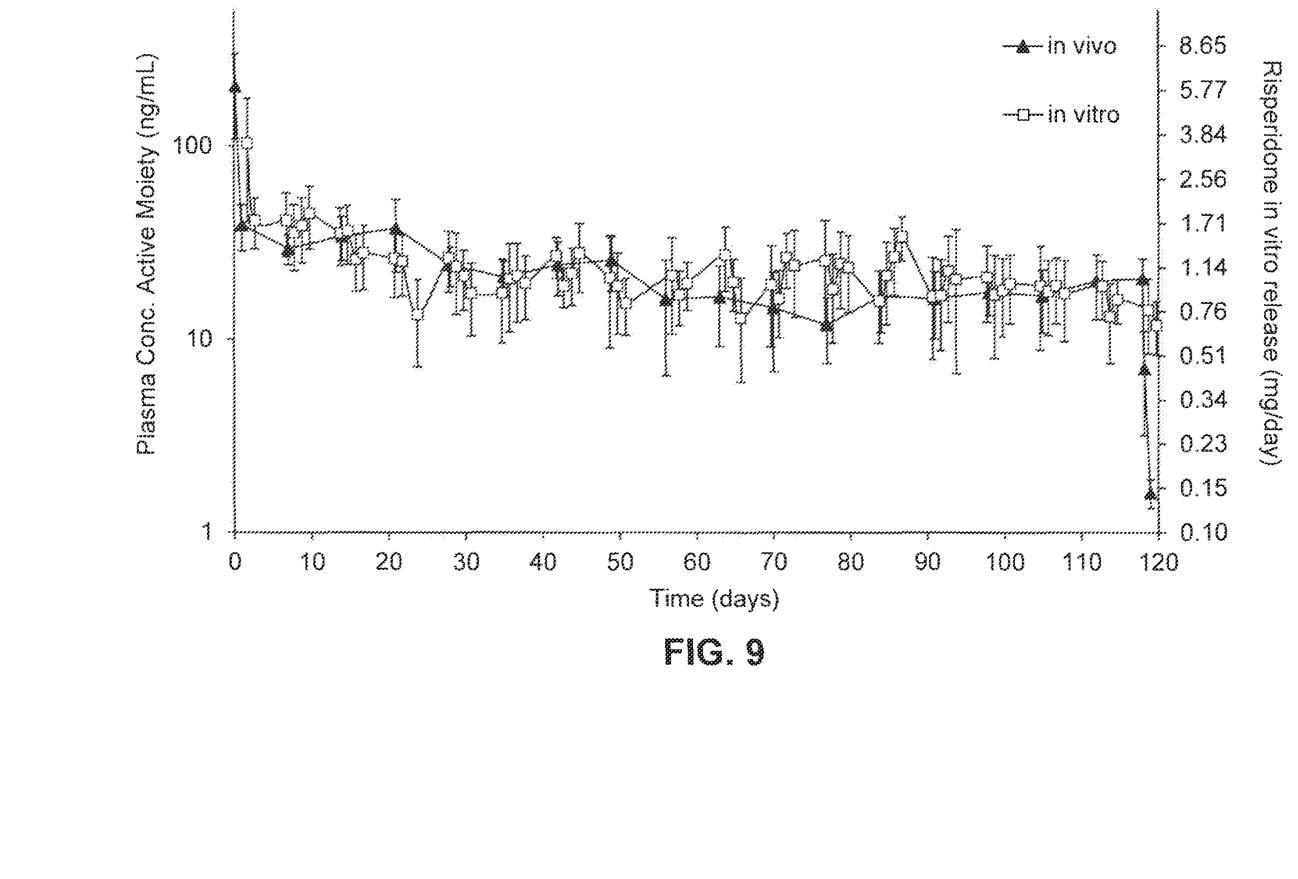
FIG. 9 is a plot showing the correlation of in vitro release and in vivo release for devices comprising the same formulation (risperidone hexanoate) and device configuration, where the in vivo release (triangles) of risperidone, in ng/mL, and the in vitro release (squares) of risperidone as a function of time, in days, is shown.

FIG. 9 is a plot showing the correlation of in vitro release and in vivo release for devices comprising the same formulation (risperidone hexanoate) and device configuration, where the in vivo release (triangles) of risperidone, in ng/mL, and the in vitro release (squares) of risperidone as a function of time, in days, is shown. The in vitro release data is from the device identified as number 180 presented in FIG. 5, and the in vivo pharmacokinetic data is that measured from devices of the same formulation and configuration implanted into rats presented in FIG. 7. There is a correlation between the two curves indicating an in vitro/in vivo correlation. Such a relationship shows that the in vitro release assay is relevant to the in vivo operation of this combination device, is valuable in predicting device performance in vivo derived from in vitro release data Based on the foregoing, it will be appreciated that the devices described herein can be used for the sustained delivery of water-insoluble drugs. In one embodiment, the water-insoluble drug is an antipsychotic agent (neuroleptic agent) used for the treatment of subjects suffering from mental disorders. Subjects with mental disorders, such as schizophrenia, bipolar disorder, psychotic depression, or Tourette's syndrome, are treated by implanting subcutaneously a device comprising a salt form of the water-insoluble drug, where the salt form of the drug provides a constant, substantially zero-order release of the drug for an extended period of between 1-6 months, or 2-6 months, or 3-6 months.

EXAMPLES

The following examples are provided to demonstrate and illustrate certain embodiments and aspects of the compositions and methods disclosed herein, but are not to be construed as limiting the scope of the claims.

Example 1

Preparation of Salt Form of a Therapeutic Agent

Risperidone (1.231 g.; 3 mmol) was dissolved in a minimal amount (about 5 mL) of dichloromethane. To this solution was added a 3 mmol aliquot of an appropriate aliphatic acid (for example, 348.5 mg or 0.375 mL of hexanoic acid). The resulting solution was mixed by transfer pipet until clear, and then evaporated to yield the desired salt. In the case of highly crystalline salts (e.g., the hexanoate), the resulting solid was first ground by mortar and pestle and then sieved to yield a powder consisting of about 20-100 µm particles, which could then be dried in vacuo to remove traces of additional solvent. In the case of soft, semi-crystalline salts (e.g., the octanoate or 2-propylpentanoate [valproate]), the resulting mixtures were loaded directly into devices as a paste. Risperidone tartrate was prepared by combining risperidone base with a stoichiometric amount of 2,3-dihydroxysuccinic acid in an appropriate solvent and removing the solvent under vacuum.

Example 2

Loading of Salt Form of Agent into Drug Delivery Devices

Cylindrical titanium reservoirs with an outer diameter (OD) of 5.4 mm, and inner diameter (ID) of 3.7 mm and a length of 40 mm were created by lathing and drilling titanium metal stock (Sorenson Precision, Inc., Goleta, Calif.). The outer diameter of each reservoir (5.5 mm form each end) was further lathed to an OD of 4.95 mm to serve as the receptive surface for the press fitting of end caps.

Reservoir caps of an OD of 5.54 mm, ID of 4.94 mm and length of 6.10 mm were milled from solid PEEK material. A 1 mm lip with an ID of 3.7 mm was incorporated in one end of the cap to serve to retain the membrane stack and o-ring during press fitting operations. Both titanium and PEEK are know to be biocompatible. Both titanium reservoirs and plastic caps were first cleaned with aqueous detergent and ethanol and then dried carefully prior to device assembly.

Each reservoir was capped at one end with an open polyether ether keton (PEEK) cap, a silicone O-ring and a porous partition by hand pressing the cap onto each end of titanium reservoir. The porous partition was sintered titanium flit with a pore size less than 5 microns.

Singly capped devices were weighed and tared on a conventional laboratory balance. The open end of each device was fitted with a small funnel, and each salt form of drug to be tested was loaded into the reservoir in small (about 10-about 50 mg) portions. When necessary, each added portion of solid was tamped down to the base of the reservoir prior to the next addition. This process was repeated until a specific loading target was met (generally about 250-500 mg). The filled reservoir was then capped with either a closed PEEK cap or a cap configuration identical to that used on the first end of the device, vide supra.

The assembled devices were weighed and then loaded into a custom-built vacuum hydrator. The air space within each device was evacuated by placing the device in a vacuum (<0.5 torr) for no less than 30 min. The devices were then back-filled with phosphate-buffered saline (pH 7.4) applied with a back pressure of 5-10 psi above atmospheric pressure for at least one hour. The devices were then retrieved from the hydration apparatus, wiped with a tissue to absorb any external fluid, weighed, and transferred to petri dishes containing buffer for the drug output assay, vide infra. The success of the hydration step was determined by the measuring the increase in mass before and after hydration.

Example 3

In Vitro Release Assay

Following hydration (Example 2), each device was transferred to a labeled petri dish containing 13 mL of Earle's balanced salt solution plus 0.02% sodium azide. The dish was placed in an incubator with $pCO_2$ adjusted to give an average buffer pH of 7.4. Approximately once per day, the dishes were retrieved from the incubator. Each device was transferred to a new dish containing an equivalent amount of buffer and then returned to the incubator.

The retained receiving buffer samples were acidified with 3.0 mL of 0.1 M HCl and allowed to stand for approximately 1 hour. An aliquot of each sample (generally 100 µL) was transferred to a single well of a UV-transparent 96 well plate along with 100 μL of 0.1 M HCl diluent. After plating, the absorbance of each well was recorded at 270 nm using a Molecular Devices spectrophotometer. The absorbances were converted into concentrations (and ultimately output mass per day) by comparison to a standard curve. Samples that absorbed outside of the linear range of the instrument were diluted and re-read, as appropriate.

Comparative Example 4

Devices with Salt Forms of Risperidone

The butanoate, benzoate, valproate and tartrate salts of risperidone free base were created as described in Example 1 and loaded and into the reservoir of devices as detailed in Example 2. In vitro release of these three preparations was measured as described in Example 3. Results are presented in FIGS. 1 and 2. As shown in the figures, and as discussed above, the release rate of risperidone tartrate falls well below the level needed to sustain therapy (0.8 mg/day). The in vitro release of the valproate, benzoate and butyrate salt forms of the drug fall below the minimum therapeutic concentration in less than 40 days and are therefore of little clinical value for the intended long-term maintenance therapy of patients with schizophrenia and bipolar disorder.

Example 5

Devices with Salt Forms of Risperidone

The pentanoate, hexanoate, and octanoate salts of risperidone free base were created as described in Example 1 and loaded and into the reservoir of devices according to the procedure detailed in Example 2. In vitro release of risperidone from the devices was measured as described in Example 3 and the results are presented in FIGS. 3 and 4. The in vitro release of the hexanoate and octanoate salts is maintained within the therapeutic concentration window (0.8 mg/day to 2.5 mg/day) for ≥60 days (FIG. 3). The in vitro output from devices loaded with risperidone pentanoate is slightly above the therapeutic window for the first 2 weeks and thereafter the output falls within the therapeutic window for up ≥60 days (FIG. 4).

Example 6

Devices with Salt Forms of Risperidone

Four groups of implant devices (designated 172, 180, 360 and 364) containing the risperidone hexanoate powder prepared and loaded as described in Examples 1 and 2 were followed for in vitro release for 90-100 days using the in vitro release assay described in Example 3. The in vitro release results are plotted in FIG. 5. As can be seen from these data, the devices released risperidone within the therapeutic range for ≥90 days.

Example 7

Devices with Salt Forms of Risperidone

Implant devices containing the risperidone hexanoate powder prepared and loaded as described in Examples 1 and 2 were followed for in vitro release for 6 months using the in vitro release assay described in Example 3. The in vitro release results are plotted in FIG. 6. As can be seen from these data, the device released risperidone at a constant rate within the therapeutic range for 6 months.

Example 8

In Vivo Pharmacokinetics

A powder intermediate of the salt of risperidone hexanoate and risperidone pentanoate were prepared as described in Example 1. Devices were filled with 290-300 mg of the risperidone hexanoate or with risperidone pentanoate powder under aseptic conditions as described in Example 2.

Six male Sprague Dawley rats (Charles River; Hollister, Calif.) of an initial weight of approximately 250-280 grams were administered a device as a subcutaneous implant. This study complied with all applicable sections of the Final Rules of the Animal Welfare Act regulations (9 CFR), the Public Health Service Policy on Humane Care and Use of Laboratory Animals, the Guide for the Care and Use of Laboratory Animals. Duration of the implantation period was 119 days. All animals were weighed and the hair was clipped and removed from the dorsal area prior to dose administration. All animals were anesthetized with isoflurane via an induction chamber and maintained in the appropriate plane of anesthesia using isoflurane inhalant (1-3%) and a vaporizer. The dorsal area of the animal was prepared for implantation using appropriate surgical scrub and ethanol. Aseptic technique was used during implantation. A small incision was made in the skin and a single device implant gently placed in the dorsal subcutaneum using a sterile implanter tool. Following administration, the skin incision was closed with sterile suture. The animals were given an appropriate dose of analgesia (see table below) and allowed to recover.

The 4-hour (day 118) and 24-hour (day 119) post-implant removal time points were the final time points (terminal time points) of the pharmacokinetic sequence and cardiac puncture was used to collect the samples. The animals were euthanized following the blood collection.

All animals were observed at least once daily for viability and general signs of health. Implantation sites were observed at least once daily for signs of infection or local reaction. Body weights were measured on the day of test article administration and weekly thereafter.

Blood for pharmacokinetic samples were collected via tail vein according to the schedule presented in the table below. Blood volumes of approximately 0.8 to 1.0 mL were collected at each time point, placed into Vacutainer tubes containing EDTA, and kept on wet ice until processing. For preparation of plasma, tubes were mixed by gentle inversion several times and centrifuged under refrigeration (approximately 2-8° C.) for approximately 15 minutes at approximately 2800 rpm (~1000×g). Plasma was split into two approximately equal aliquots and transferred to labeled screw-top tubes for storage, and stored at approximately (−60° C. to −80° C.) until shipment to the analytical lab.

| | Post-Implantation | | | | | | | | | | | | | | | | | | Post-Implant Removal | |
|---|---|---|---|---|---|---|---|---|---|---|---|---|---|---|---|---|---|---|---|---|
| | Day 0 | | DAY | | | | | | | | | | | | | | | | Day 118 | 119 |
| Time | 4 hr | 24 hr | 7 | 14 | 21 | 28 | 35 | 42 | 49 | 56 | 63 | 70 | 77 | 84 | 91 | 98 | 105 | 112 | 118 Implant Removal | +4 hr | +24 hr |
| # animals | 3 | 3 | 6 | 6 | 6 | 6 | 6 | 6 | 6 | 6 | 6 | 6 | 6 | 6 | 6 | 6 | 6 | 6 | 6 | 3 | 3 |

After 118 days of observation, all animals were anesthetized with a cocktail of Ketamine/Xylazine/Acepromazine (1.0 mL/kg IM) per Pacific Biolabs, Inc. SOP. Using aseptic technique, the implant site was opened up and a photo of the implant field was taken. Blood draws were made four hours and 24 hours after implant removal. Any observations were recorded. The implant site was examined and showed no evidence of inflammation or other adverse tissue responses. In the case of devices loaded with risperidone pentanoate, the same protocol was followed and plasma active moiety (risperidone plus 9-hydroxyrisperidone) concentration was measured up to day 91. Post-explantation plasma concentrations were not measured.

Bioanalytical measurements of active moiety (risperidone+9-OH risperidone) were conducted by Integrated Analytical Solutions (Berkeley, Calif.) using an LCMS method validated to resolve risperidone and 9-OH risperidone in rat plasma with a lower limit of quantitation (LLQ) of 0.5 ng/mL for each analyte.

Plasma concentrations were normalized to initial body weight for each time point and plotted versus time. Results are shown in FIGS. 7-8. Following a small burst of drug at the 4 hour time point, the plasma level of active moiety (risperidone plus 9-OH risperidone) remained constant at about 20 ng/mL for 118 days (FIGS. 7, 8). Following removal of the device, the plasma level immediately fell to below the LLQ (0.5 ng/mL).

Example 9

In Vitro—In Vivo Correlation

In FIG. 9 the in vitro release data from the device identified as number 180 presented in FIG. 5 is compared with the in vivo pharmacokinetic data measured from devices of the same formulation and configuration implanted into rats presented in FIG. 7. As can be seen there is a significant correlation between the two curves indicating an in vitro/in vivo correlation. Such a relationship shows that the in vitro release assay is relevant to the in vivo operation of this combination device, is valuable in predicting device performance in vivo derived from in vitro release data, and is viewed favorably by regulatory authorities for assessing device refinements and process optimization.

While a number of exemplary aspects and embodiments have been discussed above, those of skill in the art will recognize certain modifications, permutations, additions, and sub-combinations thereof. It is therefore intended that the following appended claims and claims hereafter introduced are interpreted to include all such modifications, permutations, additions and sub-combinations as are within their true spirit and scope.

What is claimed is:

1. A drug delivery device, comprising:
   a non-erodible, non-porous housing member defining a reservoir, said housing member having first and second opposing ends;
   a porous partition positioned in the housing member; and
   contained within said reservoir, a drug formulation comprised of a salt form of risperidone selected from the group consisting of risperidone octanoate, risperidone hexanoate and risperidone pentanoate, wherein the drug formulation when hydrated releases risperidone at a rate that provides a therapeutic dose over a period of at least about 2 months.

2. The device according to claim 1, wherein the therapeutic dose is between about 0.8-2.5 mg/day.

3. The device according to claim 2, wherein risperidone is released at a substantially zero-order rate of release.

4. The device of claim 1, wherein the porous partition is positioned in one or both ends of the housing member.

5. The device of claim 1, wherein the housing member is a cylindrical titanium tube and the porous partition is positioned at both ends of the reservoir.

6. A method for extended delivery of risperidone to a subject in need of treatment, comprising implanting a device according to claim 1.

* * * * *